United States Patent [19]
Fitchett et al.

[11] Patent Number: 5,912,031
[45] Date of Patent: Jun. 15, 1999

[54] PROCESS FOR PREPARING A FAT REPLACER BY ENZYMATIC DIGESTION OF A GROUND CEREAL WITH ALPHA-AMYLASE

[76] Inventors: Colin Stanley Fitchett, 13 Sedgwick St., Cambridge, United Kingdom, CB1 3AJ; Philip Ross Latham, 18 Howard Close, Cambridge, United Kingdom, CB5 8QU

[21] Appl. No.: 08/722,193
[22] PCT Filed: Apr. 10, 1995
[86] PCT No.: PCT/GB95/00816
  § 371 Date: Dec. 20, 1996
  § 102(e) Date: Dec. 20, 1996
[87] PCT Pub. No.: WO95/27407
  PCT Pub. Date: Oct. 19, 1995

[30] Foreign Application Priority Data

Apr. 11, 1994 [GB] United Kingdom .................. 9407104

[51] Int. Cl.⁶ .................................................. A23L 1/105
[52] U.S. Cl. ............................... 426/18; 426/52; 426/804
[58] Field of Search ........................ 426/18, 19, 20, 426/804, 52

[56] References Cited

U.S. PATENT DOCUMENTS

| | | | |
|---|---|---|---|
| 3,950,543 | 4/1976 | Buffa et al. | 426/18 |
| 4,299,848 | 11/1981 | De Stefanis | 426/20 |
| 4,448,790 | 5/1984 | Sarkki | 426/18 |
| 5,082,673 | 1/1992 | Inglett | 426/21 |
| 5,225,219 | 7/1993 | Inglett | 426/28 |
| 5,246,718 | 9/1993 | Haring | 426/18 |
| 5,330,779 | 7/1994 | Watanabe | 426/19 |
| 5,387,426 | 2/1995 | Harris | 426/18 |
| 5,395,640 | 3/1995 | Harris | 426/18 |
| 5,409,726 | 4/1995 | Stanley | 426/578 |
| 5,436,019 | 7/1995 | Harris | 426/578 |
| 5,651,828 | 7/1997 | Whistler | 426/28 |
| 5,711,986 | 1/1998 | Chiu | 426/549 |

FOREIGN PATENT DOCUMENTS

| | | | |
|---|---|---|---|
| 0120724 | 7/1987 | European Pat. Off. | A23J 1/12 |
| 0231729 | 8/1987 | European Pat. Off. | C12P 19/14 |
| 0141602 B1 | 2/1991 | European Pat. Off. | C12P 19/20 |
| 0453390 B1 | 1/1994 | European Pat. Off. | A23L 1/105 |
| 0577294 A2 | 1/1994 | European Pat. Off. | A23L 1/308 |
| 2134767 | 8/1984 | United Kingdom | A23K 1/14 |
| WO89/02705 | 4/1989 | WIPO | A23L 1/105 |
| WO89/10970 | 11/1989 | WIPO | C12P 19/14 |
| WO90/15147 | 12/1990 | WIPO | C12P 19/14 |
| WO91/01091 | 2/1991 | WIPO | A23L 1/0522 |
| WO91/03543 | 3/1991 | WIPO | C12F 1/00 |
| WO91/07106 | 5/1991 | WIPO | A23L 1/308 |
| WO92/10106 | 6/1992 | WIPO | A23L 1/105 |
| WO93/09244 | 5/1993 | WIPO | C12P 19/14 |
| WO93/10675 | 6/1993 | WIPO | A23L 1/09 |
| WO94/00025 | 1/1994 | WIPO | A23L 1/164 |

*Primary Examiner*—Carolyn Paden
*Attorney, Agent, or Firm*—Testa, Hurwitz & Thibeault LLP

[57] ABSTRACT

The invention relates to a process for preparing a food ingredient suitable for use as a fat replacer, the process comprising the steps of: (a) forming an aqueous slurry of ground cereal, the slurry having a dry solids content of 10 to 50 weight percent; (b) enzymatically digesting the slurry at 60–95° C. with an α-amylase enzyme capable of being deactivated by temperatures below 100° C., whereby the enzymatic digestion is effected without any significant protein degradation; and (c) thermally deactivating the α-amylase enzyme. The products of this process are useful as fat replacers in a wide variety of foods, including baked products, dairy products and meat products. Also disclosed is the use of certain products as fat replacers in food.

14 Claims, 2 Drawing Sheets

PROCESS FOR PREPARING A FAT REPLACER BY ENZYMATIC DIGESTION OF A GROUND CEREAL WITH ALPHA-AMYLASE

BACKGROUND OF THE INVENTION

The present invention relates to a process for the preparation of food ingredients by enzymatic digestion of cereals. More particularly, the invention relates to the enzymatic solubilisation under controlled conditions of the starch component of ground cereal, especially wheat flour. Products made according to the process of the invention contain a high concentration of dextrins together with finely dispersed protein, and are useful as fat replacers in the food industry, for example in baked products (e.g. cakes), dairy products and meat products.

It is known to degrade cereal products with starch- and/or protein-degrading enzymes under various conditions. The products of such degradation, or "digestion", depend on many factors, including the identities of the starting material (s) and enzyme(s) used, and the temperature, pH and substrate concentration in the material to be digested.

U.S. Pat. No. 5,225,219 discloses a process in which an aqueous slurry of a finely milled cereal is digested with an α-amylase enzyme ("G-Zyme G995" or "Taka-lite") at a pH of 5.5–7.5 and at a temperature of 60–100° C., preferably 95° C., for a period generally of 1–10 minutes. The enzyme is then inactivated by heating to 140° C. under pressure, or by acidification at pH 3.5–4.0 at 95° C. for about 10 minutes. The soluble fraction is separated from the insoluble residue by filtration or centrifugation. A substantially pure amylodextrin composition is then extracted from the water-soluble fraction by precipitation using a water-miscible organic solvent, e.g. ethanol.

The medical problems (notably heart disease) which may result from a diet high in fats, particularly saturated fats, are well documented. Consequently, the food industry has expended much effort in searching for alternatives to fats as food ingredients. Depending on the application, such fat replacers must fulfil certain requirements relating inter alia to their physico-chemical behaviour in the foods concerned and to their palatability. A wide variety of fat replacers is available, including purified dextrins, which may be obtained according to the process in the aforementioned U.S. patent.

SUMMARY OF THE INVENTION

We have now surprisingly found that by using particular conditions when digesting an aqueous slurry of a ground cereal with an α-amylase enzyme, the starch component of the cereal can be degraded in order to produce a product containing comparatively high concentrations of dextrins together with finely dispersed protein. The product has properties which make it highly suitable for use as a fat replacer in food, without further refining steps such as those taught in the aforementioned U.S. patent.

According to one aspect of the present invention, we therefore provide the use as a fat replacer in food of the product of a process comprising the steps of:

(a) forming an aqueous slurry of ground cereal, the slurry having a dry solids content of 10 to 45 weight percent;

(b) enzymatically digesting the slurry at 60–95° C. with an α-amylase enzyme, whereby the enzymatic digestion is effected without any significant protein degradation; and (c) deactivating said α-amylase enzyme;

whereby said product is not subjected to further refining steps prior to said use. An important feature is that the protein content of said product is not removed prior to said use.

The ground cereal used in the process may be any cereal commonly employed in the art, for example wheat, oats, barley, rice, maize and sorghum. Wheat flour is the preferred ground cereal for the process.

The preferred temperature for the enzymatic digestion is 65–85° C., more preferably around 70° C. Proceeding with the digestion at these moderate temperatures allows the process to be more accurately controlled, so that the product contains the desired substances, notably dextrins. Dextrins are intermediate products obtained in the transformation of starches into maltose and d-glucose. Complete digestion of starches by α-amylases leads to maltose. This disaccharide may be degraded to the monosaccharide glucose in known manner using amyloglucosidase enzymes at lower pH (around 4.0–5.0).

Deactivation of the enzyme in step (c) of the above process is preferably effected by raising the temperature of the slurry to a suitable level. However, deactivation may also be accomplished by any other method known in the art, e.g. reducing pH. A combination of approaches, e.g. low pH and high temperature, may also be used.

In the products produced by the above process, the starch component of the ground cereal is degraded under such conditions that a moderately high proportion of dextrins is obtained. A suitable time period for such digestion depends upon the temperature used, but is typically less than 1 hour, and may be less than 10 minutes. In the process, there is no significant degradation of the cereal proteins. We have found that some products of the above process possess a creamy texture, which we surmise results from the presence in the product of a combination of a high proportion of soluble dextrins and finely dispersed cereal protein. Purified dextrins available commercially do not possess this creamy texture. The products of the process may also readily be dried to a powder, e.g. by spray-drying in known manner. The products produced according to the above process preferably contain at least 30 weight % soluble dextrins, based on the weight of the solids in said products. More preferably, said products contain at least 50 weight % soluble dextrins.

We have found, by means of HPLC analysis, that products obtained according to a process having a short digestion time contain a comparatively high ratio of high molecular weight maltodextrins to lower molecular weight maltodextrins. Products with this high ratio have been found to spray-dry more readily. On the other hand, more complete digestion of the starches in the cereal gives rise to a sweeter product, having a high DE (Dextrose Equivalent) value. A longer period of digestion may therefore be desired if a sweeter product is required.

The above process may employ any α-amylase enzyme which is active under the conditions specified for the digestion. It is advantageous to use α-amylases referred to as 1,4-α-D-glucan glucanohydrolases (EC 3.2.1.1.). One such enzyme, "Termamyl" (obtainable commercially from Novo Nordisk, Denmark), has high thermal stability, i.e. its activity is destroyed only by exposure to temperatures in excess of 110° C. This enzyme is known in the art for degrading starch to maltose under more severe conditions than those employed in the above process. In the above process, it is preferred to use an α-amylase enzyme which is capable of being deactivated at temperatures below 100° C. Processes utilizing such an enzyme are novel and inventive per se, and constitute a further aspect of the invention.

Thus, according to a further aspect of the present invention, we provide a process for preparing a food ingredient suitable for use as a fat replacer, said process comprising the steps of:

(a) forming an aqueous slurry of ground cereal, the slurry having a dry solids content of 10 to 50 weight percent;

(b) enzymatically digesting the slurry at 60–95° C. with an α-amylase enzyme capable of being deactivated by temperatures below 100° C., whereby the enzymatic digestion is effected without any significant protein degradation; and (c) thermally deactivating said α-amylase enzyme.

A preferred α-amylase enzyme suitable for use in the process of the invention is BAN (Bacterial Amylase Novo, commercially available from Novo Nordisk, Bagsvaerd, Denmark). This is a 1,4-α-D-glucan glucanohydrolase which is produced by submerged fermentation of a selected strain of *Bacillus amylolichuefaciens*. BAN has its maximum activity between 60 and 80° C., and may be inactivated within 15 minutes at a temperature of 95° C.

The use in the present invention of enzymes with lower thermal stability results in a saving in energy (and hence an economic saving) when the enzyme is inactivated. The lower inactivation temperature also substantially avoids the occurrence of browning in the product. Browning occurs to a greater degree above 100° C., and is undesirable in some food products since it may adversely affect not only the appearance but also the flavour. Some browning may also be due to caramelisation of sugars in the mixture being digested. Caramelisation affects the flavour of the product, and may also have health implications. BAN, the preferred enzyme for the process of the invention, can be rapidly inactivated at temperatures in excess of 90° C.

In carrying out the process of the invention, it is generally unnecessary to regulate the pH of the aqueous slurry, e.g. by adding alkali or acid as in many known digestion processes. This is because the natural pH's of aqueous slurries of ground cereals are also the pH's at which many suitable α-amylase enzymes function satisfactorily. For example, the pH of an aqueous slurry of wheat flour is approximately 6.2, the precise figure depending upon the wheat flour source and concentration in the slurry. The proteins naturally present in the wheat flour are not degraded during the digestion process, and act as a buffer. BAN enzyme has its optimal activity at pH 5 to 7.

According to one embodiment of the invention, ground cereal, e.g. wheat flour is dispersed at between 10 and 45 weight percent solids in water which has been preheated to a temperature between 60 and 95° C. α-amylase enzyme is added to this slurry, and solubilises the starch. It is preferred to subject the slurry to agitation during the digestion process. Methods for doing this are known in the art. For example, slurry may be subjected to high shear via an overhead homogeniser in the digestion tank and/or an in-line homogeniser. According to this embodiment of the invention, the temperature of the digest is steadily raised from the initial temperature to reach between 90 and 100° C. at the end of the incubation. The enzyme activity is then destroyed by maintaining the mixture at this final temperature for approximately 10 minutes.

The enzyme dosage, the temperature profile of the digestion process and the duration of the digestion can be varied depending upon the dextrin composition and degree of digestion and sweetness required in the final product. If convenient, the product of the digestion process may be used in the liquid/gel form. Generally, it is preferred to dry the product to a powder by a known method such as spray-drying, integrated belt drying or drum drying.

DESCRIPTION OF THE PREFERRED EMBODIMENTS

Figure 1:
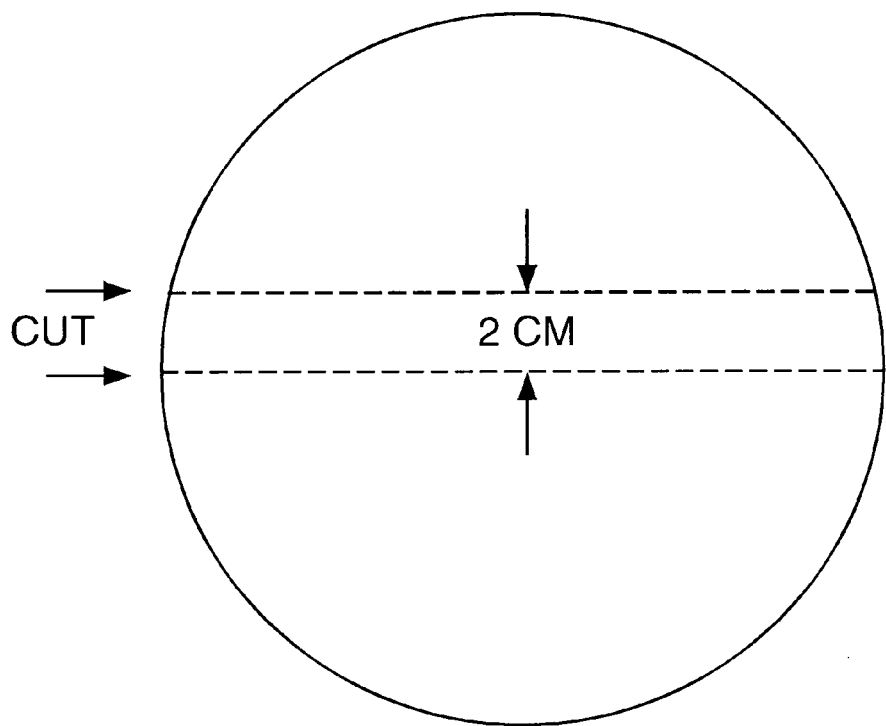
FIG. 1 illustrates the section of cake used for the purpose of rheological testing of cakes prepared as described in Example 4 hereinafter.

For a better understanding of the invention, the following non-limiting Examples are provided by way of illustration.

EXAMPLE 1

Wheat flour (which typically comprises 10 weight percent protein) is dispersed in water to give an aqueous slurry at 85° C. having a dry solids content of 33 weight percent. A white flour is employed, e.g. having a 75% extraction rate in milling. BAN 240L (Novo Nordisk) is added at 0.02% of the flour weight. The temperature of the digest is raised to 95° C. in 10 minutes and held at that temperature for 10 minutes. The wet slurry is allowed to cool and is recovered as a waxy, greasy solid with a fat-like texture. If desired, the product may be dried to yield a free-flowing powder. This process leads to a product having a Dextrose Equivalent (DE) of less than 3 and with the following constituents (all figures in weight percent, based on the weight of solids in the product):

| Protein | 10 |
| --- | --- |
| Soluble dextrins | 50 |
| Maltose | 2 |
| Glucose | <1 |

EXAMPLE 2

Wheat flour as in Example 1 is dispersed in water to give a 33 weight percent slurry at 75° C. BAN 240L (Novo) is added at 0.02% of the flour weight. The temperature of the digest is raised to 95° C. over a period of 30 minutes, and held at that temperature for 15 minutes in order to inactivate the enzyme. The product has a DE of below 12, and can be dried to yield a free-flowing powder. A typical analysis, in weight % based on the weight of the solids, is as follows:

| Protein | 10 |
| --- | --- |
| Soluble dextrins | 65 |
| Maltose | 3 |
| Glucose | <1 |

EXAMPLE 3

Wheat flour as in Example 1 is dispersed in water to give a 33 weight percent slurry at 68° C. BAN 240L enzyme (Novo) is added at 0.04% of the flour weight. The temperature of the digest is raised to 95° C. over a period of 50 minutes and held at that temperature for 15 minutes. The product typically has a DE of 33 and the following constituents, in weight % based on the weight of the solids:

| | |
|---|---|
| Protein | 10 |
| Soluble dextrins | 30 |
| Maltose | 40 |
| Glucose | <1 |

Products of the process of the invention are suitable for use as fat replacers. Their ability to be dried to a powder makes them particularly suitable for use in food products derived substantially from dry ingredients, e.g. cakes and other baked products. The dry powder may itself be incorporated in the recipe, where appropriate, or it may be reconstituted to a liquid/gel with water prior to mixing with other ingredients.

According to another aspect of the invention, we therefore provide the use of the product of a process of the invention as a fat replacer in a food product. According to a further aspect of the invention we provide the use of the product of a process of the invention as a fat replacer in a cake recipe.

As mentioned above, the products produced by processes described herein have use as fat replacers in a wide variety of foods, including baked products, dairy products and meat products. The following non-limiting Examples are intended to illustrate the fat replacement properties of such a product in cake and in soup.

EXAMPLE 4

A conventional Devon Sponge recipe was used to evaluate the fat replacement properties of a product of the invention having a Dextrose Equivalent (DE) of 9. For convenience, this product is henceforth referred to as "Product A".

In the standard recipe, the dry ingredients contain 16% fat. Several fat-free recipes were evaluated in which the fat was replaced with varying proportions of N-Flate, water, flour, Product A or a combination of BV40 with either flour or Product A. Table 1 shows which of these ingredients were used instead of the fat in the various recipes. N-Flate is a known, commercially available (National Starch Co.) fat replacer specially adapted for use in cake recipes.

N-Flate consists of emulsifiers glycerol monostearate (GMS) and polyglycerol esters (PGE), guar, starch and skimmed milk powder. BV40 is a known emulsifier mix (available from DMV B.V., Vegkel, Netherlands) which contains GMS, PGE and acetic acid ester.

In the preparation of the sponges, the dry ingredients were pre-blended. In the control recipe, the fat was then rubbed in; in the other recipes, the ingredients used instead of the fat were incorporated at the stage appropriate to non-fat materials. N-Flate and BV40 were used in accordance with the manufacturers' instructions. Increased levels of water were required in the fat-free recipes, relative to the control, and this water was incorporated when the first water addition was made. All recipes were carried out in duplicate.

After baking, all cakes were allowed to cool for at least one hour prior to rheological testing. A 2 cm slab was then cut from the cake as illustrated in FIG. 1, the first of the two cuts being that passing through the

TABLE 1

Cakes prepared (Devon Sponge) for the evaluation of fat replacers

Figure 2:
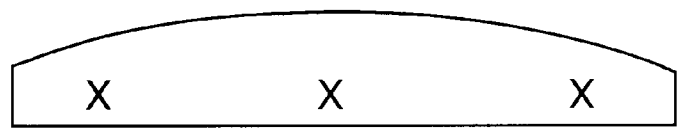
FIG. 2 shows the positions on the sectioned cake slab which were subjected to rheological testing as described in Example 4 hereinafter.
Figure 3:
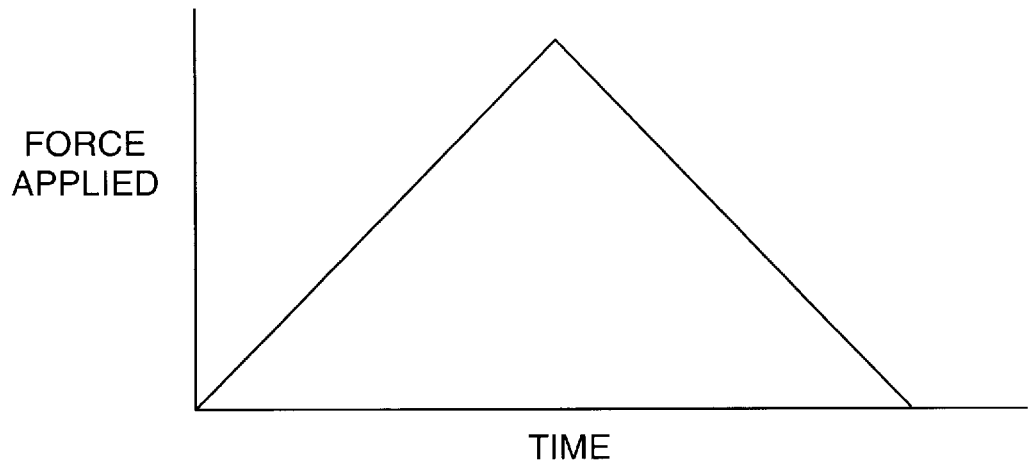
FIG. 3 shows the variation of loading force applied to the cake slab with time according to the rheological test carried out as described in Example 4 hereinafter.
Figure 4:
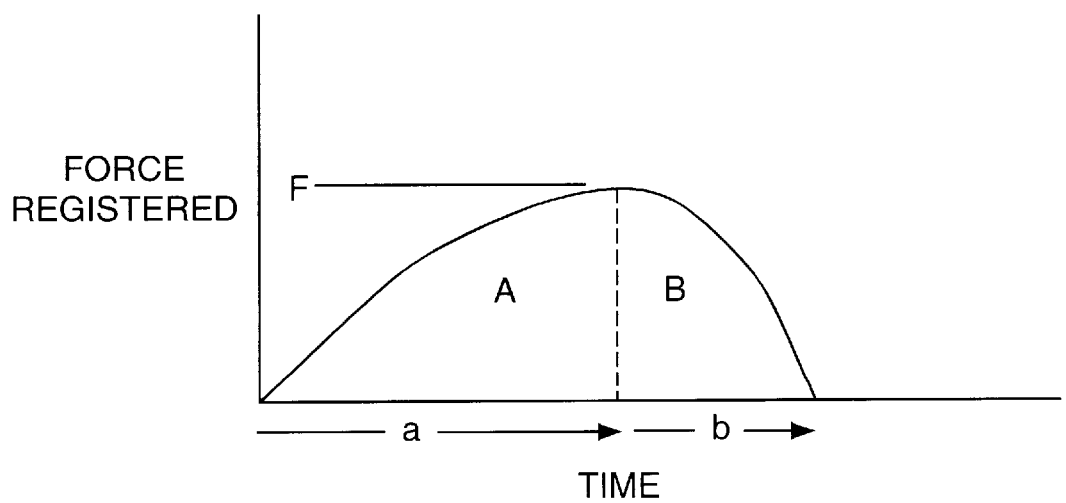
FIG. 4 shows a typical loading profile of a cake slab tested in accordance with the method described in Example 4 hereinafter.

| Number | Fat replacers | Level of fat replacer relative to fat (%) | Energy of fat or of fat replacer (kcal/g) |
|---|---|---|---|
| 1 | Fat (16%), Control | — | 9 |
| 2 | N-Flate | 50 | 2.5 |
| 3 | Water | 100 | 0 |
| 4 | Flour | 25 | 1 |
| 5 | Flour | 50 | 2 |
| 6 | Product A | 25 | 1 |
| 7 | Product A | 50 | 2 |
| 8 | Flour:BV40 (3:1) | 50 | 2.2 |
| 9 | Product A:BV40 (3:1) | 50 | 2.2 | centre of the cake. The slab was then tested at the positions shown in FIG. 2. Using an Instron Materials Tester, a 1.5 cm diameter probe was gently lowered onto the upper surface of the cake until a 0.1N force was registered. The instrument was then reset to zero, and the probe was depressed 5 mm into the cake at a rate of 50 mm per minute, before retracting the probe at the same rate. The variation of applied force with time is shown schematically in FIG. 3. The force registered was taken as an indication of crumb firmness. A measure of the loading and unloading behaviour was also recorded, giving an indication of the flow properties of the crumb; a typical trace is shown in FIG. 4. The force F is the maximum load registered, whilst a and b represent the loading time and unloading time registered. Area A represents the total loading force registered, and area B the total unloading force.

Of particular note is the quality of "shortness", as governed by the presence of fat. A short, friable crumb tends to disintegrate upon compression, and thus is associated with a low elasticity value and a high hysteresis value (see FIG. 4).

To give an indication of cake volume, the cross-sectional area was calculated. Sectioned cakes were photocopied, and the paper impression was cut out with scissors. The paper was then weighed, allowing the cross-sectional area to be calculated according to the known mass of paper.

Table 2 provides a summary of the results of cake assessment. Crumb firmness (N) corresponds to level F in FIG. 4. Elasticity varies from 0% (no elasticity) to 100% (full elasticity of crumb structure), and is defined as 100×b/a. Hysteresis varies from 0% (no energy loss) to 100% (full energy loss from crumb flow), and is defined as 100×(1−B/A).

TABLE 2

| Number | Fat replacers | Cross-sectional area (cm$^2$) | Crumb Firmness (N) | Elasticity (%) | Hysteresis (%) | Crumb Appearance |
|---|---|---|---|---|---|---|
| 1 | Fat (Control) | 46 | 0.64 | 36 | 89 | Fine-structured |
| 2 | N-Flate | 50 | 0.60 | 49 | 79 | Fine-structured |
| 3 | Water | 40 | 0.99 | 69 | 68 | Open-structured |
| 4 | Flour (25%) | 42 | 0.82 | 67 | 70 | Open-structured |
| 5 | Flour (50%) | 46 | 0.96 | 73 | 66 | Open-structured |

TABLE 2-continued

| Number | Fat replacers | Cross-sectional area (cm²) | Crumb Firmness (N) | Elasticity (%) | Hysteresis (%) | Crumb Appearance |
|---|---|---|---|---|---|---|
| 6 | Product A (25%) | 43 | 0.63 | 62 | 71 | Intermediate quality |
| 7 | Product A (50%) | 52 | 0.44 | 53 | 72 | Fine-structured |
| 8 | Flour:BV40 (3:1) | 47 | 0.79 | 65 | 69 | Fine-structured |
| 9 | Product A:BV40 (3:1) | 47 | 0.45 | 42 | 81 | Fine-structured |

Replacement of fat with the known fat replacer N-Flate gave cakes of similar volume, crumb firmness and crumb appearance to the control but led to an increase in crumb elasticity and a decrease in hysteresis. This is believed to be associated with a diminution of the shortness of the crumb. Nevertheless, cakes containing water alone or flour alone (i.e. cakes 3,4 and 5) were of much lower shortness (as judged by elasticity and hysteresis).

Inclusion of Product A at the lower level (cake 6) provided only limited influence on the textural properties of cake as compared with flour alone (cake 4), but at the higher level there was a marked influence on all the textural parameters relative to cake where flour was used for fat replacement (compare cakes 5 and 7). Moreover, Product A at the higher level gave a degree of functionality similar to the known fat replacer N-Flate.

With regard to the inclusion of the BV40 in blends with flour or Product A, (cakes 8 and 9) the most notable influence was an increase in crumb shortness (as judged by elasticity and hysteresis) relative to cakes containing flour or Product A alone. Moreover, the blend containing Product A and BV40 was of superior functionality to the known fat-replacer N-Flate.

It can be seen from the above that Product A has highly effective functionality as a fat replacer in cake. Furthermore, its combination with suitable emulsifiers may bring about particularly advantageous results.

EXAMPLE 5

A standard dry soup formulation was used to test the fat replacement suitability of products produced by processes according to the invention. Three products P, Q and R were manufactured according to the processes of Examples 1, 2 and 3 respectively. These products were then incorporated in soup recipes having a conventional formulation but from which the fat normally present had been omitted. A negative control, in which the fat was replaced by dextrin, was also employed for comparison. The formulations used were as follows (all ingredients in weight %):

| FORMULATION | | | |
|---|---|---|---|
| | Standard | Fat-replaced | Negative control |
| Spray-dried fat | 19 | — | — |
| Product (P or Q or R) | — | 5* | — |
| Starch | 14 | 18 | 14 |
| Wheat Flour | 20 | 23 | 20 |
| Flavourings | 8 | 8 | 8 |
| Dextrin (DE15) | 6 | 8 | 25 |
| Salt, sugar and seasonings | 4 | 4 | 4 |
| Skimmed milk powder | 29 | 34 | 29 |

*In the case of Product P, only 0.7% by weight was employed, the balance being water.

The soups were reconstituted by combining one part of the above formulations with two parts of water (by weight). The soups were then cooked and served to a Taste Panel. The standard recipe soup as served had a fat content of 6.5% by weight, whilst the fat-replaced soup had a fat content of only 0.3% by weight.

The soups were assessed by a Taste Panel the members of which were asked to rank the soups on the basis of perceived creaminess. The results were interpreted using the known Friedman Rank Test: a low R-value indicates a high ranking, and a difference of greater than 15.6 in this test indicates a significant difference between the test materials at 99.9% confidence level.

| Soup | R-value |
|---|---|
| P | 28 |
| Q | 17 |
| R | 23 |
| Standard | 44 |
| Negative control | 51 |

It can be seen that the Taste Panel ranked the Fat-replaced soups higher than the Standard soup for creaminess at the 99.9% confidence level. The difference between the fat-replaced products was not significant.

We claim:

1. A process for preparing a food ingredient suitable for use as a fat replacer, said process comprising the steps of:
   (a) forming an aqueous slurry of ground cereal, the slurry having a dry solids content of about 10 to 45 weight percent;
   (b) adding an α-amylase enzyme capable of being deactivated at temperatures below 100° C. to said slurry so as to enzymatically digest said slurry, whereby the enzymatic digestion is effected without any significant protein degradation; and
   (c) deactivating said α-amylase enzyme by heating at a temperature below 100° C. and not at pH 3.5–4.0, whereby the resulting material is used as a fat replacer without any further processing.

2. A process as claimed in claim 1, characterized in that the ground cereal is wheat flour.

3. A process as claimed in claim 1, characterized in that in step (b) the enzymatic digestion is effected at 65–85° C.

4. A process as claimed in claim 1, characterized in that the α-amylase enzyme is a 1,4-α-D-glucan glucanohydrolase.

5. A process as claimed in claim 4, characterized in that the 1,4-α-D-glucan glucanohydrolase is obtained from *Bacillus amylolichuefaciens*.

6. A process as claimed in claim 1, characterized in that the slurry is subjected to agitation during the digestion process.

7. A food ingredient obtainable by the process of claim 1.

8. A process as claimed in claim 3, wherein said enzymatic digestion is effected at 70° C.

9. A food ingredient for use in food, said food ingredient being produced by a process comprising the steps of:

(a) forming an aqueous slurry of ground cereal, the slurry having a dry solids content of 10 to 45 weight percent;
(b) adding an α-amylase enzyme capable of being deactivated at temperatures below 100° C. to said slurry so as to enzymatically digest said slurry and thereby form said food ingredient, whereby the enzymatic digestion is effected without any significant protein degradation; and
(c) deactivating said α-amylase enzyme by heating at a temperature below 100° C. and not at pH 3.5–4.0,
wherein said food ingredient is not subjected to further refining steps prior to said use.

10. The food ingredient of claim 9, characterized in that the ground cereal is wheat flour.

11. The food ingredient of claim 9, characterized in that the α-amylase enzyme is a 1,4-α-D-glucan glucanohydrolase.

12. The food ingredient of claim 9, characterized in that said food ingredient contains at least 30 weight % soluble dextrins.

13. The food ingredient of claim 9, comprising a fat replacer.

14. A food ingredient as claimed in claim 12, wherein said food ingredient used contains at least 50 weight % soluble dextrins.

* * * * *